United States Patent [19]

Martinez et al.

[11] Patent Number: 4,919,653

[45] Date of Patent: Apr. 24, 1990

[54] DEVICE FOR LOCATING THE EPIDURAL SPACE

[76] Inventors: Antonio E. Martinez; Eduardo C. Garcia, both of Cea Bermudez 31 - 50B, 28001 Madrid, Spain

[21] Appl. No.: 219,219

[22] Filed: Jul. 13, 1988

[30] Foreign Application Priority Data

Jul. 28, 1987 [ES] Spain ............................... 8702216

[51] Int. Cl.$^5$ .............................................. A61M 5/00
[52] U.S. Cl. .................................. 604/117; 604/164; 128/748
[58] Field of Search ............... 604/117, 118, 164, 165, 604/158; 128/673–675, 748

[56] References Cited

U.S. PATENT DOCUMENTS

| | | | |
|---|---|---|---|
| 4,356,826 | 11/1982 | Kubota | 604/117 X |
| 4,535,773 | 8/1985 | Yoon | 604/118 |
| 4,801,293 | 1/1989 | Jackson | 604/117 |

Primary Examiner—Stephen C. Pellegrino
Attorney, Agent, or Firm—Zarley, McKee, Thomte, Voorhees & Sease

[57] ABSTRACT

The device for locating the epidural space being proposed is based on the depression existing at that space. It consists of a circuit and a canula with a corresponding coaxial needle. Once the circuit is energized, a puncture is carried out with the canula up to the surroundings of the yellow ligament. The canula is fixed at this position by means of a fixer element which is displaced along the canula up to the patient's back. The needle is inserted into the canula and by careful manual force or punching it continues until reaching the epidural space. When that happens, the circuit is triggered due to the existing depression at the epidural space, one or more alarms or signals and an electromagnet being thereby activated, the latter attracting the needle and a sleeve into which it is coaxially positioned. By frictional engagement to one another, the needle and sleeve move farther through the canula in response to the activated electromagnet. With the simultaneous displacement of the sleeve and of the needle, the needle reaches the center of the epidural space, situated 2 mm away from the circuit triggering position, this being the maximum sleeve displacement distance.

6 Claims, 8 Drawing Sheets

DEVICE FOR LOCATING THE EPIDURAL SPACE

The present invention, as expressed by the title of this specification, refers to a device for locating the epidural space, so as to introduce into it anaesthetics, analgesics, narcotics, etc., by injection with a needle or a catheter.

This space corresponds to that between both leaves of the dura mater, inside the rachitic duct and extends itself along it from the occipital hole up to the sacrococcygeal hiatus.

The current method for locating the epidural space is based on the sanitary technician's skill. The reduced size of this space, varying depending on multiple factors, such as: age, sex, weight, body size, etc., as well as its differences with respect to that portion of the spinal column which is intended to be blocked, make the current methods be rather rudimentary and dangerous, since the punching of the dura mater may produce a continuous loss of cephalorachitic fluid with the subsequent occurrence of hypotension in cavities containing said fluid and, as a consequence thereof, headaches and even paralysis when pressure fall is very sharp.

In order to improve the guarantees of success of anaesthesias of this type, avoiding to the maximum extent the above mentioned complications, the present invention proposes a device based on the characteristics that the epidural space possesses a depression. Said device consists of a canula and a needle which inserted into the former, said needle having a vacuum inlet in contact with a pressure sensor that transforms the pressure signal into an electrical signal which is received by an integrated circuit (comparator), wherein it is compared with the atmospheric pressure, When the end of the needle reaches the epidural space, the circuit is closed by a transistorized switch, so that an electromagnet situated at the canula handle is activated, said electromagnet diametrically attracting the needle (of ferromagnetic material), and introducing it into a rear sleeve the inner surface of which is corrugated, just as the outside of the needle is in a portion of length. Just at the same moment as the electromagnet is activated, a visual and/or sound alarm is activated so as to advise the user on the moment when the epidural space is contacted. At this moment, the user makes the needle pierce through by means of the sleeve, which has a maximum displacement of 2 mm, this being the distance at which the centre of the epidural space is away. Afterwards, any substance can be injected or a catheter can be introduced.

The device comprises:

A pressure sensor that transforms the pressure signal into an electric signal.

An adjustable voltage divider in order to be able to equalize the voltage with that of tthe pressure sensor.

A millivoltmeter in order to graphically see the difference between both above voltages.

An integrated circuit.(comparator) that emits a signal when there is a difference between the aforementioned voltages.

A transistorized switch that closes the circuit when receiving the signal from the comparator.

All necessary circuit protection elements against voltage picks and induced currents.

A buzzer and a lamp or led diode which become activated when the circuit is closed by the transistorized switch.

A support canula of whichever external shape and provided with a handle inside which there are an electromagnet, a stop and a sleeve which can axially move in the distance determined by said stop, being equivalent to 2 mm.; the sleeve is of plastic material or of any other non-ferromagnetic material, with a very smooth outer finish and a corrugated inner finish so that the needle being displaced inside it is easily blocked against it. This sleeve is limited by a stop that enables it to have a 2 mm maximum displacement.

A fixation element constituted by a flat body of resilient material, provided with two unidirectional fixation flanges.

A conically pointed needle without sharp edges so that when it penetrates it separates tissue fibres without cutting, the latter returning to their position by elasticity as the needle is taken out, thereby producing the least traumatism as possible.

Said needle must be made of a ferromagnetic material (for instance, chromium-vanadium steel) and the part opposing the point must have a corrugated outer finish that enables it to be easily blocked against the sleeve.

The rear part of the needle is welded to a conical body, generally of plastic material, provided with a cut whereto a wing nut can be coupled, the latter serving as support for safer and easier puncture, and with a cut whereto the connector indicating the situation of the needle opening is coupled. The connector for vacuum inlet is situated at the rear part, with some grooves in its outside for easier handling.

Once the circuit has been connected by a hand switch, a puncture is carried out with the canula up to the surroundings of the yellow ligament, being fixed at this position by means of the fixation element that is displaced up to the patient's back. The needle is introduced into the canula and it goes on with the puncture, up to reaching the epidural space, when the circuit is triggered due to the existing depression, the alarms and the electromagnet being thereby activated, the latter attracting the needle and inserting it into the sleeve. With the simultaneous displacement of the sleeve and the needle, the centre of the epidural space, situated 2 mm away, is reached, this being the distance to which the sleeve can displace itself.

The device can also be used without the mechanical blocking of the support canula, allowing oneself to be guided by the acoustic and/or optical alarms and, moreover, if the existing vacuum is not intended to be measured, the circuit can be substituted by a membrane which, when being displaced due to the vacuum, closes the alarm circuit.

For a better comprehension of this specification and as an integral part thereof, some drawing sheets are attached thereto, wherein their different figures represent, with an illustrative but not-limiting character, the following:

Figure 1:
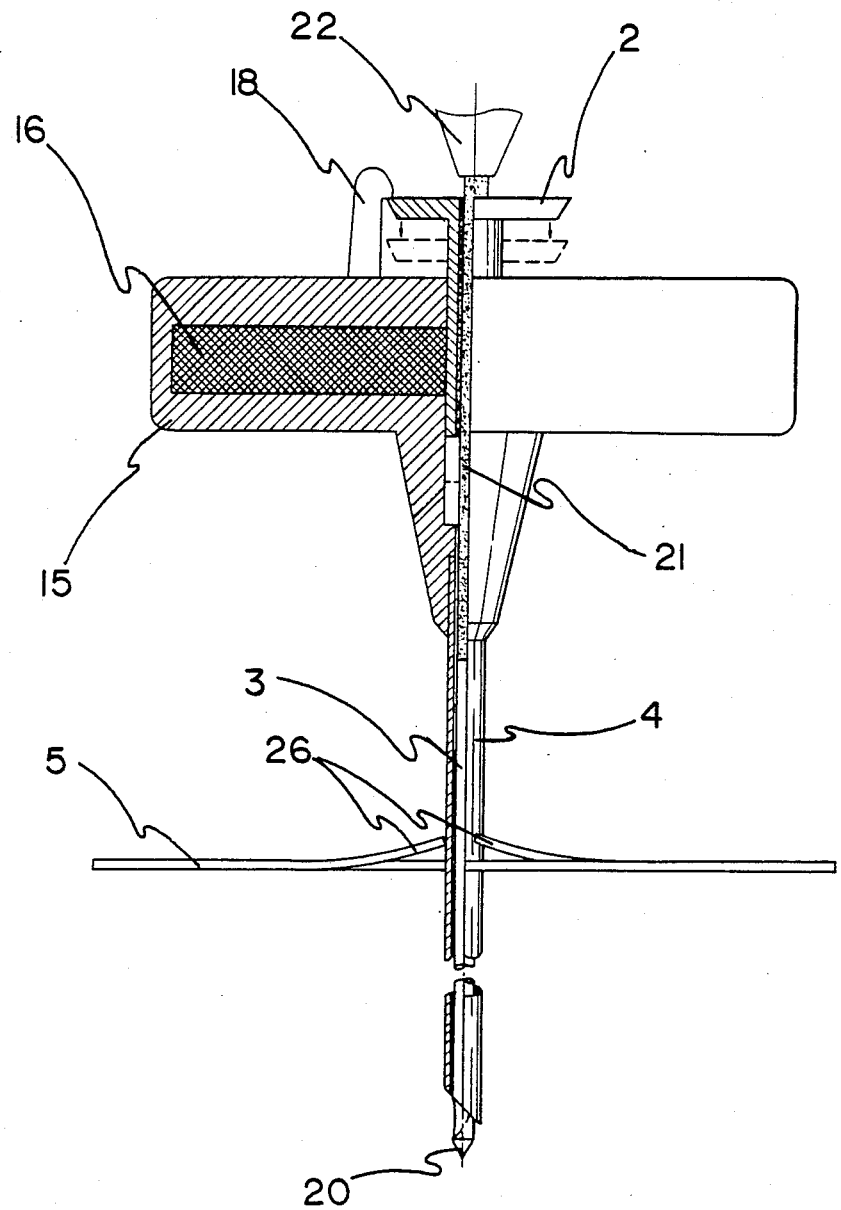
FIG. 1 is an elevational view, with a one-fourth section, of the device according to th invention.

Reference being made to the above mentioned figures, it can be seen that the device for locating the epidural space proposed by the invention consists of a canula 1, at the rear part of which there is a sleeve 2, the needle 3 being introduced through them. Along the tube 4 of the canula a unidirectional fixation element 5 can be displaced.

Figure 2:
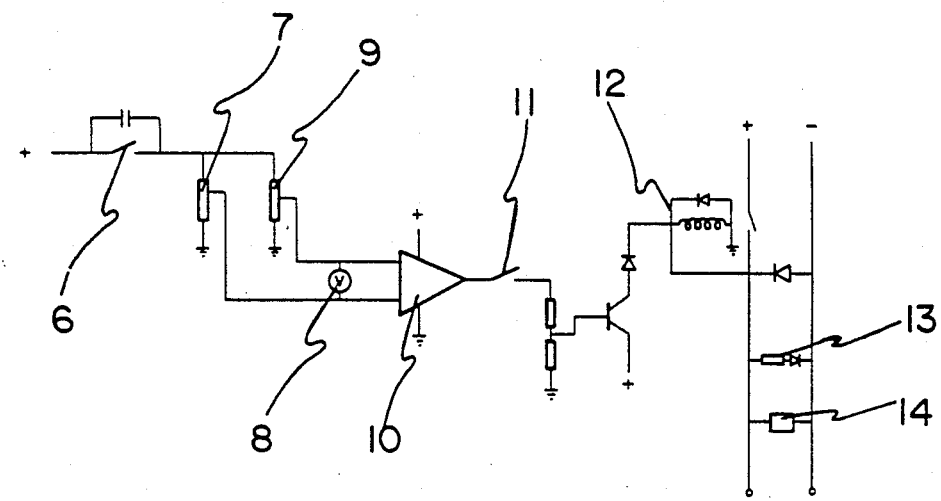
FIG. 2 is a schematic view of the circuit of the device according to FIG. 1.
Figure 3:
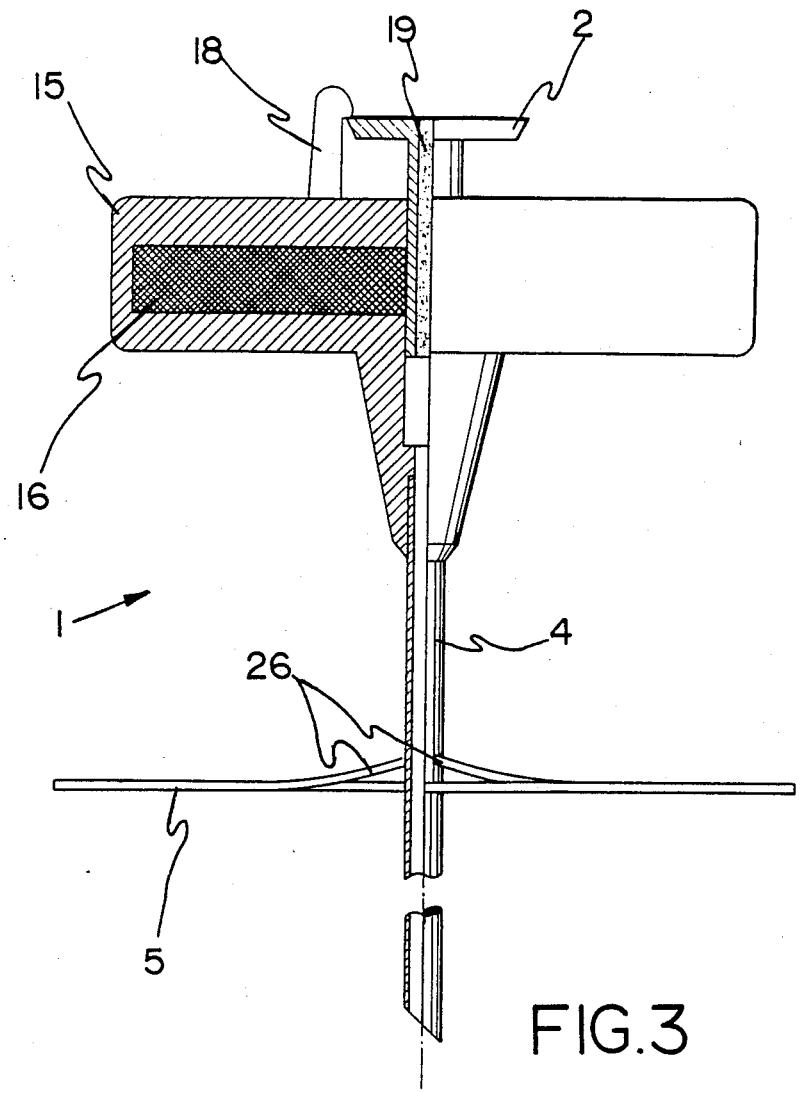
FIG. 3 is an elevational view of the canula according to FIG. 1.
Figure 4:
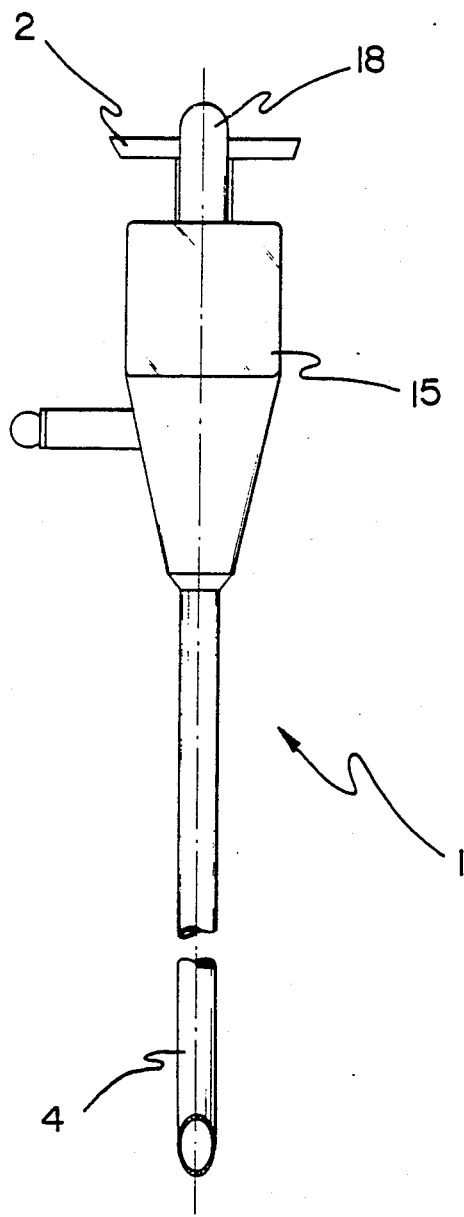
FIG. 4 is a ground view of the canula according to the previous Figure.

The electric circuit as represented in FIG. 2 is constituted by a hand switch 6, a voltage divider 7, a millivoltmeter 8, a pressure sensor 9, a comparator 10, a switch 11 at said comparator outlet, a relay 12 and the luminous 13 and acoustic 14 alarms.

The canula 1 is constituted by the support body 15 and the tube 14. Inside said support body, there is an electromagnet 16 surrounding the axial sleeve 2, situated at the rear part of the support body 15. This sleeve may gently displace itself up to a maximum of 2 mm., this distance being regulated by the stop 18. The inner surface 19 of the sleeve is considerably corrugated.

The needle 22 has a conical point 20 without sharp edges, so that when it is introduced it separates the tissue fibres apart without cutting them, thereby producing as less traumatism as possible. The outer diameter of the needle will be slightly smaller than the inner one of the tube 4 of the canula and of the sleeve 2. A portion 21 of the outer surfacee of the needle has a corrugated surface complementary to the inner surface 19 of the sleeve.

The rear part of the needle is welded to a conical body 22 provided with a cut 23 whereto a wing nut (not shown) can be coupled serving as support for the technician's fingers to manually puncture and punch easily and safely the needle up to the surroundings of the yellow ligament. The vacuum inlet 24, besides some grooves 25 for an easier handling, is situated at the rear part.

The fixation element 5 is constituted by a flat body of elastic material, provided with two unidirectional fixation flanges 26.

The device as described in the preceding paragraphs works as follows:

The circuit is connected by the hand switch 6. A puncture is performed with the canula up to the surroundings of the yellow ligament, being fixed at this position by the fixation element, as it is displaced until it contacts the patient's back. Once the canula has been fixed, the axial sleeve being at its backmost position, the needle is introduced until the alarms and the electromagnet are activated, the latter attracting the needle due to the ferromagnetic condition of the material of which it is constituted, inserting it into the sleeve due to the rubbing of the corrugated surfaces in contact. With the simultaneous displacement of sleeve and needle, one reaches the epidural space centre when arriving to the anterior sleeve displacement stop. At this position, the concerned substances can be injected or the catheter can be introduced.

Figures 5, 6:
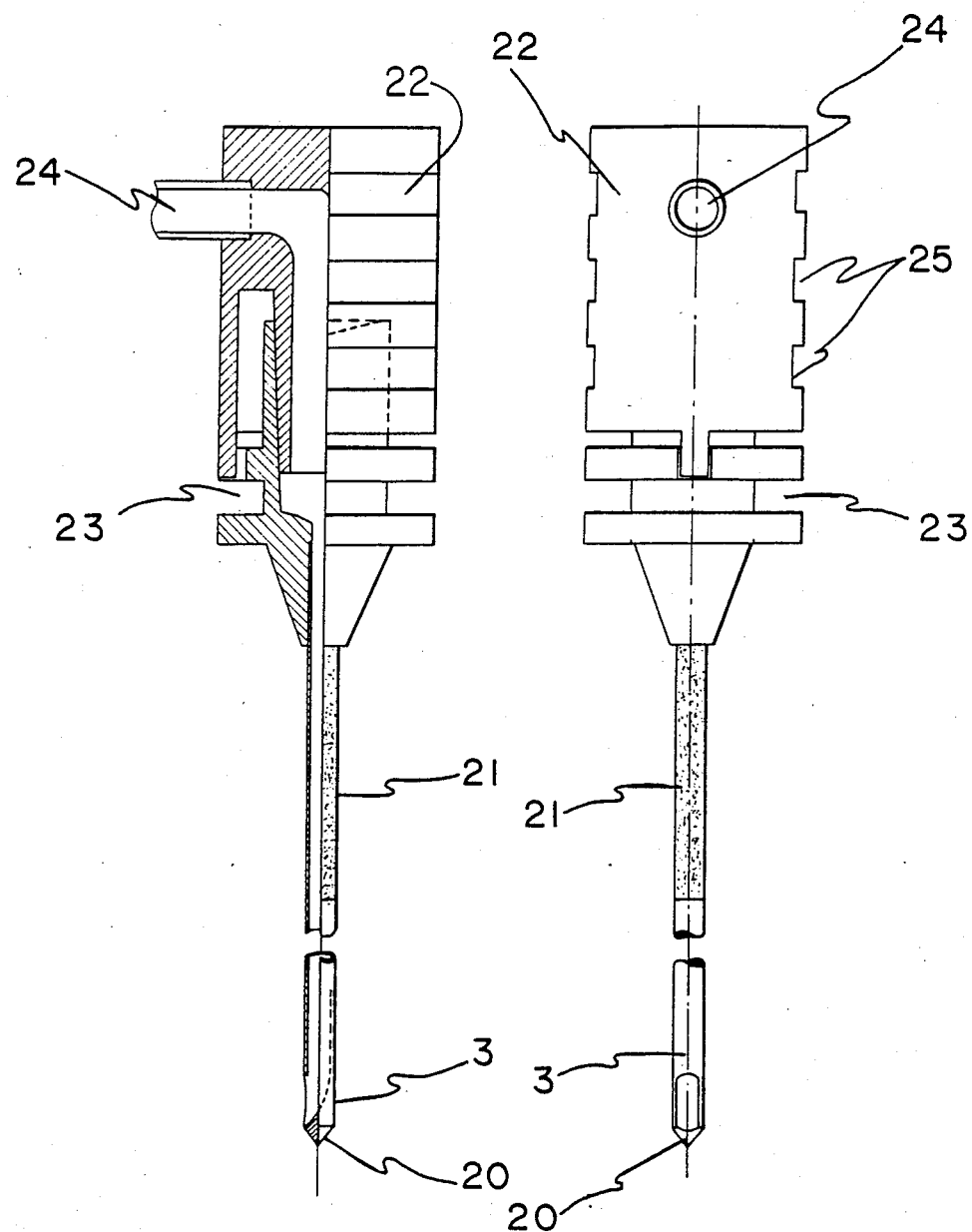
FIG. 5 is an elevational view of the needle of the device according to the5 invention.
FIG. 6 is a ground view of the needle of the previous Figure.
Figure 7:
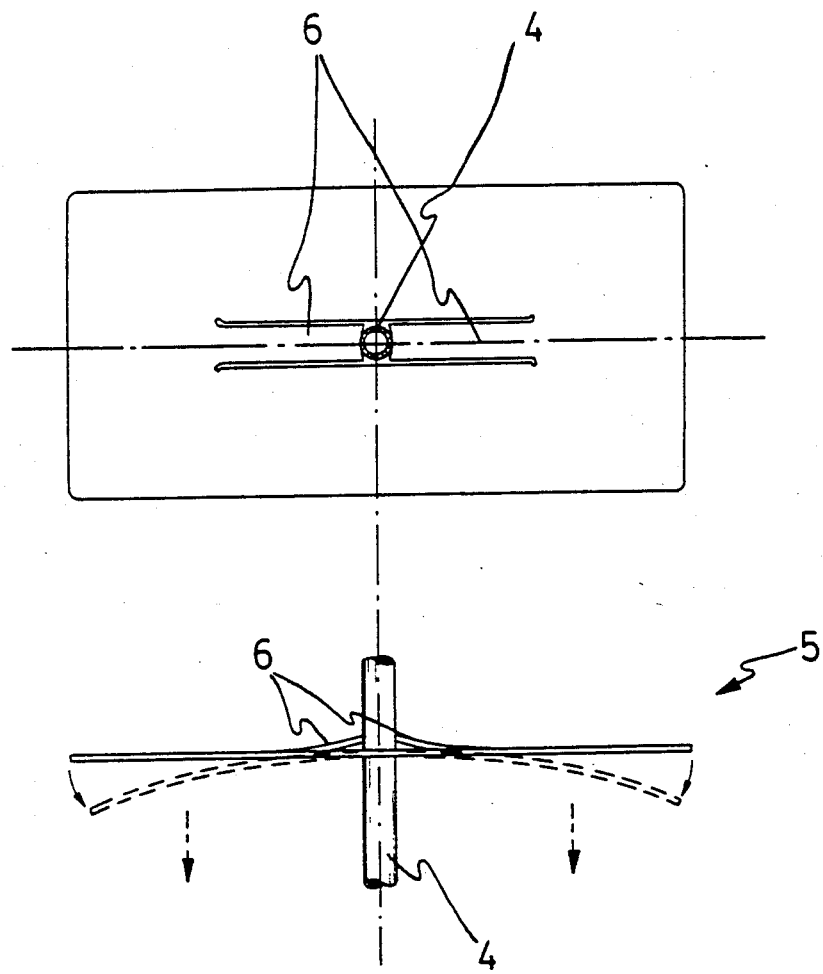
FIGS. 7a and 7b are an elevational and lateral view respectively of the unidirectional fixation element of the canula according to FIGS. 3 and 4.
Figure 7A:
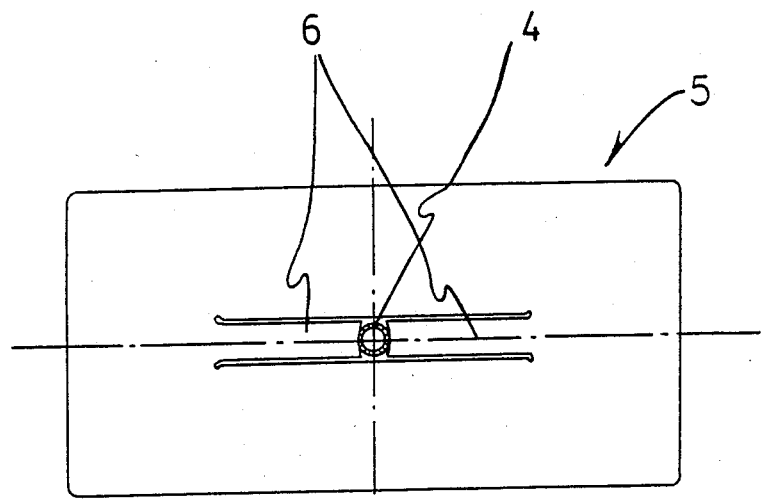
Figure 7B:
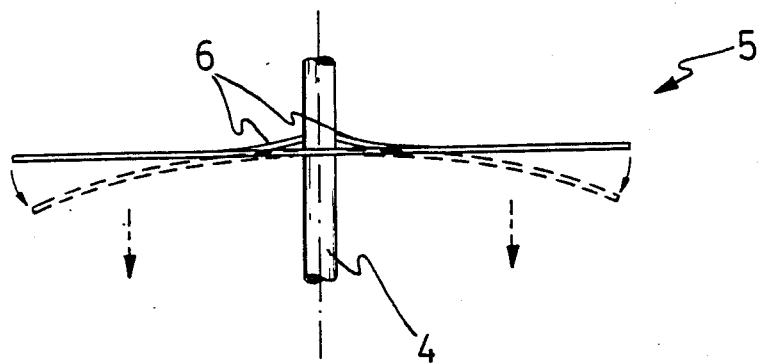

The alarms and the electromagnet become activated due to the fact that the pressure sensor detects the depression existing at the epidural space, which signal is converted into an electric signal that produced a voltage difference between the sensor and the potentiometer, this difference being annuled with observation of the millivoltmeter. FIG. 5 shows the vacuum inlet 24 in concical body 22 of needle 3, which is connected to pressure sensor 9 as shown in FIG. 2. Pressure sensor 9 senses the change in pressure at needle tip 20 and converts it to an electrical signal which activates the electromagnet and alarms, as previously described.

Figure 8:
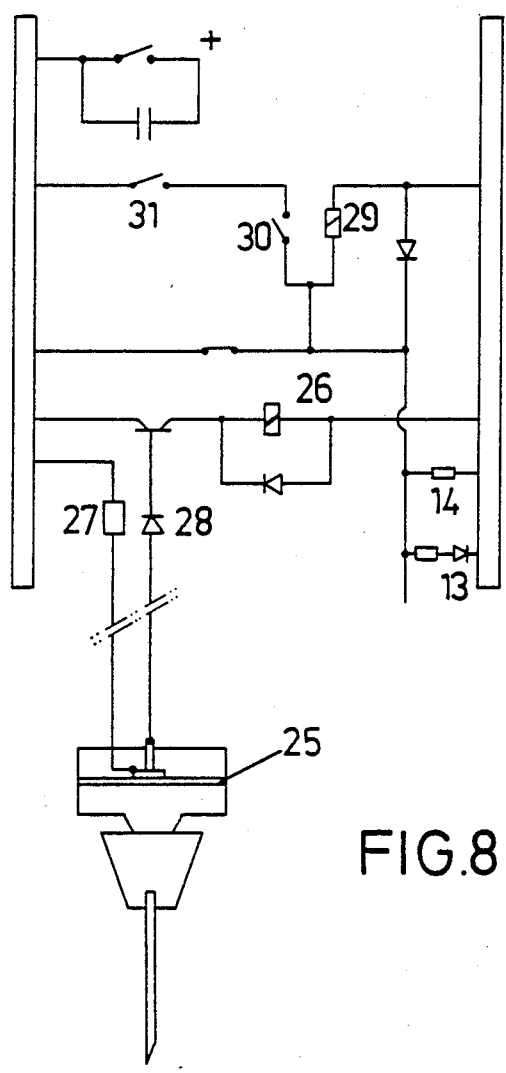
FIG. 8 is a schematic view of a second type of circuit which the device according to the invention may comprise.

FIG. 8 represents a second example of embodiment of the alarm circuit of the epidural device. In this case, the pressure sensor consists of a small membrane (25) provided with an electric contact, which is closed in the membrane resting position and open when said membrane is sucked on reaching the epidural space. The passage of current keeps the circuit open by means of a relay (26). Current intensity is low thanks to the fact that the circuit comprises a resistor (27).

A lamp (28) can be kept on meanwhile the epidural space is not reached, the luminous 13 and acoustic 14 alarms being then activated. The circuit may comprise some system, such as the relay (29) and the switches (30) and (31), in order to allow the alarms to keep on working, although the membrane (25) contact is closed again.

The device for locating the epidural space which has been described constitutes a revolution in anaesthesia field, as the guarantees of success have a considerable increase, since it is not required for the technicians to be so much specialized.

I claim:

1. A device for locating the epidural space, for introducing into it anesthetics, analgesics, narcotics, and the like, by injection with a needle or a catheter, essentially characterized by comprising a canula provided with a duct therethrough and a handle inside which an electromagnet is situated and at the rear part of which there is a retaining element that also works as a stop of a sleeve axially situated in the handle, the inner surface of the sleeve being considerably corrugated; the canula further including a fixation element adjustable along the canula in order to prevent the canula from penetrating beyond the yellow ligament, thereby allowing the axial and comfortable introduction through the sleeve and the canula duct of a conically pointed needle with lateral outlet, the needle having a corrugated outer surface portion capable of being inserted into the sleeve by the electromagnet action, which is activated by a circuit operatively connected to the device capable of detecting the depression existing in the epidural space by the use of a pressure sensor operatively connected to the needle, which transforms the pressure signal into an electric signal, which is passed on to an electric circuit, so that, if there is a difference between the atmospheric pressure and the detected one, a transistorized switch will close the circuit and the above mentioned electromagnet and one or both of a sound and visual alarm will be activated.

2. A device for locating the epidural space, according to claim 1, characterized in that the needle is made of ferromagnetic material, such as, for instance, chromium-vandium steel.

3. A device for locating the epidural space, according to claims 1 or 2, further comprising a needle support element, generally of plastic, which has a cut for coupling a wing nut and some outer grooves for a safer and easier puncture, the needle support element including a connector for the vacuum inlet to connect the needle with the pressure sensor.

4. A device for locating the epidural space, according to claim 1, characterized in that the circuit includes an adjustable voltage divider in order to be able to equalize the voltage with that of the pressure sensor, a millivoltmeter to control the difference between both voltages and a hand switch for operating the device.

5. A device for locating the epidural space, according to claim 1, characterized in that the pressure sensor consists of a small membrane which opens or closes the circuit that activates the alarms, as it displaces itself.

6. A device for locating the epidural space, according to claim 1, characterized in that the displacement of the needle once the epidural space has been reached, is carried out through the sleeve wherein it is inserted, said sleeve having a maximum displacement of 2 mm., which is suitable for reaching the centre of said epidural space.

* * * * *

UNITED STATES PATENT AND TRADEMARK OFFICE
CERTIFICATE OF CORRECTION

PATENT NO. : 4,919,653

DATED : April 24, 1990

INVENTOR(S) : Antonio Espejo Martinez
Eduardo Castroviejo Garcia

It is certified that error appears in the above—identified patent and that said Letters Patent is hereby corrected as shown below:

On the title page, under item [19], "Martinez" should be --Espejo Martinez--.

On the title page, in item [76] Inventors:, delete "E." and substitute therefore --Espejo--; after the inventor's name "Eduardo", please delete "C." and substitute therefore --Castroviejo--.

Signed and Sealed this

Nineteenth Day of May, 1992

Attest:

DOUGLAS B. COMER

Attesting Officer

Acting Commissioner of Patents and Trademarks